US009249208B2

(12) United States Patent
Serre et al.

(10) Patent No.: US 9,249,208 B2
(45) Date of Patent: Feb. 2, 2016

(54) CITRULLINE PEPTIDES DERIVED FROM FIBRIN AND RECOGNIZED BY RHEUMATOID ARTHRITIS SPECIFIC AUTOANTIBODIES, AND THE USE THEREOF

(75) Inventors: Guy Serre, Toulouse (FR); Mireille Sebbag, Toulouse (FR)

(73) Assignee: Biomerieux, Marcy-L'etoile (FR)

( * ) Notice: Subject to any disclaimer, the term of this patent is extended or adjusted under 35 U.S.C. 154(b) by 279 days.

(21) Appl. No.: 13/489,072

(22) Filed: Jun. 5, 2012

(65) Prior Publication Data
US 2013/0028922 A1    Jan. 31, 2013

Related U.S. Application Data

(62) Division of application No. 11/577,674, filed as application No. PCT/FR2005/002736 on Nov. 3, 2005, now Pat. No. 8,207,299.

(30) Foreign Application Priority Data

| Nov. 4, 2004 | (FR) | 04 11782 |
| Dec. 22, 2004 | (FR) | 04 13711 |
| Aug. 8, 2005 | (FR) | 05 08422 |

(51) Int. Cl.
*C07K 14/75* (2006.01)
(52) U.S. Cl.
CPC ..................................... *C07K 14/75* (2013.01)
(58) Field of Classification Search
None
See application file for complete search history.

(56) References Cited

U.S. PATENT DOCUMENTS

2007/0009507 A1    1/2007   Serre et al.

FOREIGN PATENT DOCUMENTS

WO    WO 03/050542 A2    6/2003

OTHER PUBLICATIONS

Girbal-Neuhauser, E. et al., *The Epitopes Targeted by the Rheumatoid Arthritis-Associated Antifilaggrin Autoantibodies are Post-translationally Generated on Various Sites of (Pro)Filaggrin by Deimination of Arginine Residues*, J. Immunol, 162 (1999) 585-594.

Hida, S. et al., *Influence of Arginine Deimination on Antigenicity of Fibrinogen*, Journal of Autoimmunity 23 (2004) 141-150.

Mason-Bessiére, C. et al., *In the Rheumatoid Pannus, Anti-Filaggrin Autoantibodies are Produced by Local Plasma Cells and Constitute a Higher Proportion of IgG Than in Synovial Fluid and Serum*, Clin Exp Immunol, 119 (2000) 544-552.

Nijenhuis, S. et al., *Autoantibodies to Citrullinated Proteins in Rheumatoid Arthritis: Clinical Performance and Biochemical Aspects of an RA-Specific Marker*, Clinica Chimica Acta 350 (2004) 17-34.

Nogueira, L. et al., *Autoantibodies to Deiminated Fibrinogen Are The Most Efficient Serological Criterion for the Diagnosis of Rheumatoid Arthritis*, Arthritis Research, vol. 4, Suppl. 1, (90) Abstracts of the $22^{nd}$ European Workshop for Rheumatology Research, (2002) 2 pages.

Mason-Bessiére, C. et al., *The Major Synovial Targets of the Rheumatoid Arthritis-Specific Antifilaggrin Autoantibodies Are Deiminated Forms of the α- and β-Chains of Fibrin*, The American Associated of Immunologists, 166 (2001) 4177-4184.

Schellekens, G.A. et al., *Citrulline is an Essential constituent of Antigenic Determinants Recognized by Rheumatoid Arthritis—specific Autoantibodies*, J. Clin. Invest., vol. 101, No. 1 (Jan. 1998) 273-281.

Schellekens, G. A. et al., *The Diagnostic Properties of Rheumatoid Arthritis Antibodies Recognizing a Cyclic Citrullinated Peptide*, Arthritis & Rheumatism, vol. 43, No. 1 (Jan. 2000) 155-163.

Sebbag, M. et al., *Clinical and Pathophysiological Significance of the Autoimmune Response to Citrullinated Proteins in Rheumatoid Arthritis*, Joint Bone Spine 71 (2004) 493-502.

Serre, G. et al., *Filaggrin (Keratin) Autoantibodies*, Autoantibodies, Peter and Shoenfeld, Editors, Elsevier Science Publishers (1996) 271-276.

Tam, P. J., *Synthetic Peptide Vaccine Design: Synthesis and Properties of a High-Density Multiple Antigenic Peptide System*, Proc. Natl. Acad. Sci. USA, vol. 85 (Aug. 1988) 5409-5413.

Union, A. et al., *Identification of Citrullinated Rheumatoid Arthritis—Specific Epitopes in Natural Filaggrin Relevant for Antifilaggrin Autoantibody Detection by line Immunoassay*, Arthritis & Rheumatism, vol. 46, No. 5 (May 2002), 1185-1195.

Vincent, C. et al., *High Diagnostic Value in Rheumatoid Arthritis of Antibodies to the Stratum Corneum of Rate Oesophagus Epithelium, So-Called 'antikeratin antibodies'*, Annals of the Rheumatic Diseases, 48 (1989) 712-722.

Vincent, C. et al., *Immunoblotting Detectin of autoantibodies to Human Epidermis, Filaggrin: A New Diagnostic Test for Rheumotoid Arthritis*, The Journal of Rheumatology, 25:5 (1998) 838-846.

*Primary Examiner* — Gerald R Ewoldt
(74) *Attorney, Agent, or Firm* — Alston & Bird LLP

(57) ABSTRACT

The invention relates to novel citrulline peptides derived from fibrin α and β chains which are recognizable by specific citrulline antiprotein autoantibodies (AAPC) of a rheumatoid arthritis (PR) and to the use thereof for detecting the presence of said specific PR AAPC in a biological sample.

10 Claims, 1 Drawing Sheet

A.

SEQ ID NO : 10
```
MFSMRIVCLV LSVVGTAWTA DSGEGDFLAE GGGVRGPRVV ERHQSACKDS DWPFCSDEDW  60
NYKCPSGCRM KGLIDEVNQD FTNRINKLKN SLFEYQKNNK DSHSLTTNIM EILRGDFSSA 120
NNRDNTYNRV SEDLRSRIEV LKRKVIEKVQ HIQLLQKNVR AQLVDMKRLE VDIDIKIRSC 180
RGSCSRALAR EVDLKDYEDQ QKQLEQVIAK DLLPSRDRQH LPLIKMKPVP DLVPGNFKSQ 240
LQKVPPEWKA LTDMPQMRME LERPGGNEIT RGGSTSYGTG SETESPRNPS SAGSWNSGSS 300
GPGSTGNRNP GSSGTGGTAT WKPGSSGPGS TGSWNSGSSG TGSTGNQNPG SPRPGSTGTW 360
NPGSSERGSA GHWTSESSVS GSTGQWHSES GSFRPDSPGS GNARPNNPDW GTFEEVSGNV 420
SPGTRREYHT EKLVTSKGDK ELRTGKEKVT SGSTTTTRRS CSKTVTKTVI GPDGHKEVTK 480
EVVTSEDGSD CPEAMDLGTL SGIGTLDGFR HRHPDEAAFF DTASTGKTFP GFFSPMLGEF 540
VSETESRGSE SGIFTNTKES SSHHPGIAEF PSRGKSSSYS KQFTSSTSYN RGDSTFESKS 600
YKMADEAGSE ADHEGTHSTK RGHAKSRPVR GIHTS                            635
```

B.

SEQ ID NO : 11
```
MKRMVSWSFH KLKTMKHLLL LLLCVFLVKS QGVNDNEEGF FSARGHRPLD KKREEAPSLR  60
PAPPPISGGG YRARPAKAAA TQKKVERKAP DAGGCLHADP DLGVLCPTGC QLQEALLQQE 120
RPIRNSVDEL NNNVEAVSQT SSSSFQYMYL LKDLWQKRQK QVKDNENVVN EYSSELEKHQ 180
LYIDETVNSN IATNLRVLRS ILENLRSKIQ KLESDVSAQM EYCRTPCTVS CNIPVVSGKE 240
CEEIIRKGGE TSEMYLIQPD SSVKPYRVYC DMNTENGGWT VIQNRQDGSV DFGRKWDPYK 300
QGFGNVATNT DGKNYCGLPG EYWLGNDKIS QLTRMGPTEL LIEMEDWKGD KVKAHYGGFT 360
VQNEANKYQI SVNKYRGTAG NALMDGASQL MGENRTMTIH NGMFFSTYDR DNDGWLTSDP 420
RKQCSKEDGG GWWYNRCHAA NPNGRYYWGG QYTWDMAKHG TDDGVVWMNW KGSWYSMRKM 480
SMKIRPFFPQ Q                                                     491
```

SEQUENCE LISTING

<160> NUMBER OF SEQ ID NOS: 12

<210> SEQ ID NO 1
<211> LENGTH: 15
<212> TYPE: PRT
<213> ORGANISM: Artificial Sequence
<220> FEATURE:
<223> OTHER INFORMATION: Citrullinated peptide
<220> FEATURE:
<221> NAME/KEY: misc_feature
<222> LOCATION: (1)..(1)
<223> OTHER INFORMATION: X = citrullyl or arginyl residue
<220> FEATURE:
<221> NAME/KEY: misc_feature
<222> LOCATION: (13)..(13)
<223> OTHER INFORMATION: X = citrullyl or arginyl residue
<220> FEATURE:
<221> NAME/KEY: misc_feature
<222> LOCATION: (15)..(15)
<223> OTHER INFORMATION: X = citrullyl or arginyl residue

```
<400> SEQUENCE: 1

Xaa Pro Ala Pro Pro Ile Ser Gly Gly Gly Tyr Xaa Ala Xaa
1               5                   10                  15

<210> SEQ ID NO 2
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: misc_feature
<222> LOCATION: (3)..(3)
<223> OTHER INFORMATION: X = citrullyl or arginyl residue
<220> FEATURE:
<221> NAME/KEY: misc_feature
<222> LOCATION: (7)..(7)
<223> OTHER INFORMATION: X = citrullyl or arginyl residue

<400> SEQUENCE: 2

Gly Pro Xaa Val Val Glu Xaa His Gln Ser Ala Cys Lys Asp Ser
1               5                   10                  15

<210> SEQ ID NO 3
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: misc_feature
<222> LOCATION: (10)..(10)
<223> OTHER INFORMATION: X = citrullyl or arginyl residue
<220> FEATURE:
<221> NAME/KEY: misc_feature
<222> LOCATION: (12)..(12)
<223> OTHER INFORMATION: X = citrullyl or arginyl residue

<400> SEQUENCE: 3

Ser Gly Ile Gly Thr Leu Asp Gly Phe Xaa His Xaa His Pro Asp
1               5                   10                  15

<210> SEQ ID NO 4
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: misc_feature
<222> LOCATION: (8)..(8)
<223> OTHER INFORMATION: X = citrullyl or arginyl residue
<220> FEATURE:
<221> NAME/KEY: misc_feature
<222> LOCATION: (11)..(11)
<223> OTHER INFORMATION: X = citrullyl or arginyl residue

<400> SEQUENCE: 4

Val Asp Ile Asp Ile Lys Ile Xaa Ser Cys Xaa Gly Ser Cys Ser
1               5                   10                  15

<210> SEQ ID NO 5
<211> LENGTH: 14
<212> TYPE: PRT
<213> ORGANISM: Artificial sequence
<220> FEATURE:
<223> OTHER INFORMATION: Citrullinated peptide
<220> FEATURE:
<221> NAME/KEY: misc_feature
<222> LOCATION: (8)..(8)
<223> OTHER INFORMATION: X = citrullyl residue
```

```
<400> SEQUENCE: 5

Glu Ser Ser Arg Asp Gly Ser Xaa His Pro Arg Ser His Asp
1               5                   10

<210> SEQ ID NO 6
<211> LENGTH: 14
<212> TYPE: PRT
<213> ORGANISM: Artificial sequence
<220> FEATURE:
<223> OTHER INFORMATION: Citrullinated peptide
<220> FEATURE:
<221> NAME/KEY: misc_feature
<222> LOCATION: (8)..(8)
<223> OTHER INFORMATION: X = citrullyl residue

<400> SEQUENCE: 6

Thr Gly Ser Ser Thr Gly Gly Xaa Gln Gly Ser His His Glu
1               5                   10

<210> SEQ ID NO 7
<211> LENGTH: 14
<212> TYPE: PRT
<213> ORGANISM: Artificial sequence
<220> FEATURE:
<223> OTHER INFORMATION: Peptide citrulline
<220> FEATURE:
<221> NAME/KEY: misc_feature
<222> LOCATION: (8)..(8)
<223> OTHER INFORMATION: X = citrullyl residue

<400> SEQUENCE: 7

Glu Gln Ser Ala Asp Ser Ser Xaa His Ser Gly Ser Gly His
1               5                   10

<210> SEQ ID NO 8
<211> LENGTH: 19
<212> TYPE: PRT
<213> ORGANISM: Artificial sequence
<220> FEATURE:
<223> OTHER INFORMATION: Citrullinated peptide
<220> FEATURE:
<221> NAME/KEY: misc_feature
<222> LOCATION: (7)..(7)
<223> OTHER INFORMATION: X = citrullyl residue
<220> FEATURE:
<221> NAME/KEY: misc_feature
<222> LOCATION: (9)..(9)
<223> OTHER INFORMATION: X = citrullyl residue

<400> SEQUENCE: 8

Ser His Gln Glu Ser Thr Xaa Gly Xaa Ser Arg Gly Arg Ser Gly Arg
1               5                   10                  15

Ser Gly Ser

<210> SEQ ID NO 9
<211> LENGTH: 18
<212> TYPE: PRT
<213> ORGANISM: Artificial sequence
<220> FEATURE:
<223> OTHER INFORMATION: Citrullinated peptide
<220> FEATURE:
<221> NAME/KEY: misc_feature
<222> LOCATION: (9)..(10)
<223> OTHER INFORMATION: X = citrullyl residue
```

-continued

```
<400> SEQUENCE: 9

Thr Ile His Ala His Pro Gly Ser Xaa Xaa Gly Gly Arg His Gly Tyr
1               5                   10                  15

His His

<210> SEQ ID NO 10
<211> LENGTH: 635
<212> TYPE: PRT
<213> ORGANISM: Homo sapiens

<400> SEQUENCE: 10

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
                20                  25                  30

Gly Val Arg Gly Pro Arg Val Val Glu Arg His Gln Ser Ala Cys Lys
            35                  40                  45

Asp Ser Asp Trp Pro Phe Cys Ser Asp Glu Asp Trp Asn Tyr Lys Cys
        50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335
```

-continued

```
Gly Ser Ser Gly Thr Gly Ser Thr Gly Asn Gln Asn Pro Gly Ser Pro
                340                 345                 350

Arg Pro Gly Ser Thr Gly Thr Trp Asn Pro Gly Ser Ser Glu Arg Gly
            355                 360                 365

Ser Ala Gly His Trp Thr Ser Glu Ser Ser Val Ser Gly Ser Thr Gly
        370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
            420                 425                 430

Leu Val Thr Ser Lys Gly Asp Lys Glu Leu Arg Thr Gly Lys Glu Lys
        435                 440                 445

Val Thr Ser Gly Ser Thr Thr Thr Arg Arg Ser Cys Ser Lys Thr
    450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
        515                 520                 525

Phe Pro Gly Phe Phe Ser Pro Met Leu Gly Glu Phe Val Ser Glu Thr
    530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
        595                 600                 605

Ser Glu Ala Asp His Glu Gly Thr His Ser Thr Lys Arg Gly His Ala
    610                 615                 620

Lys Ser Arg Pro Val Arg Gly Ile His Thr Ser
625                 630                 635

<210> SEQ ID NO 11
<211> LENGTH: 491
<212> TYPE: PRT
<213> ORGANISM: Homo sapiens

<400> SEQUENCE: 11

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
        35                  40                  45

Leu Asp Lys Lys Arg Glu Glu Ala Pro Ser Leu Arg Pro Ala Pro Pro
    50                  55                  60

Pro Ile Ser Gly Gly Gly Tyr Arg Ala Arg Pro Ala Lys Ala Ala Ala
65                  70                  75                  80
```

-continued

```
Thr Gln Lys Lys Val Glu Arg Lys Ala Pro Asp Ala Gly Gly Cys Leu
                85                  90                  95
His Ala Asp Pro Asp Leu Gly Val Leu Cys Pro Thr Gly Cys Gln Leu
            100                 105                 110
Gln Glu Ala Leu Leu Gln Gln Glu Arg Pro Ile Arg Asn Ser Val Asp
        115                 120                 125
Glu Leu Asn Asn Asn Val Glu Ala Val Ser Gln Thr Ser Ser Ser Ser
    130                 135                 140
Phe Gln Tyr Met Tyr Leu Leu Lys Asp Leu Trp Gln Lys Arg Gln Lys
145                 150                 155                 160
Gln Val Lys Asp Asn Glu Asn Val Val Asn Glu Tyr Ser Ser Glu Leu
                165                 170                 175
Glu Lys His Gln Leu Tyr Ile Asp Glu Thr Val Asn Ser Asn Ile Ala
            180                 185                 190
Thr Asn Leu Arg Val Leu Arg Ser Ile Leu Glu Asn Leu Arg Ser Lys
        195                 200                 205
Ile Gln Lys Leu Glu Ser Asp Val Ser Ala Gln Met Glu Tyr Cys Arg
    210                 215                 220
Thr Pro Cys Thr Val Ser Cys Asn Ile Pro Val Val Ser Gly Lys Glu
225                 230                 235                 240
Cys Glu Glu Ile Ile Arg Lys Gly Gly Glu Thr Ser Glu Met Tyr Leu
                245                 250                 255
Ile Gln Pro Asp Ser Ser Val Lys Pro Tyr Arg Val Tyr Cys Asp Met
            260                 265                 270
Asn Thr Glu Asn Gly Gly Trp Thr Val Ile Gln Asn Arg Gln Asp Gly
        275                 280                 285
Ser Val Asp Phe Gly Arg Lys Trp Asp Pro Tyr Lys Gln Gly Phe Gly
    290                 295                 300
Asn Val Ala Thr Asn Thr Asp Gly Lys Asn Tyr Cys Gly Leu Pro Gly
305                 310                 315                 320
Glu Tyr Trp Leu Gly Asn Asp Lys Ile Ser Gln Leu Thr Arg Met Gly
                325                 330                 335
Pro Thr Glu Leu Leu Ile Glu Met Glu Asp Trp Lys Gly Asp Lys Val
            340                 345                 350
Lys Ala His Tyr Gly Gly Phe Thr Val Gln Asn Glu Ala Asn Lys Tyr
        355                 360                 365
Gln Ile Ser Val Asn Lys Tyr Arg Gly Thr Ala Gly Asn Ala Leu Met
    370                 375                 380
Asp Gly Ala Ser Gln Leu Met Gly Glu Asn Arg Thr Met Thr Ile His
385                 390                 395                 400
Asn Gly Met Phe Phe Ser Thr Tyr Asp Arg Asp Asn Asp Gly Trp Leu
                405                 410                 415
Thr Ser Asp Pro Arg Lys Gln Cys Ser Lys Glu Asp Gly Gly Gly Trp
            420                 425                 430
Trp Tyr Asn Arg Cys His Ala Ala Asn Pro Asn Gly Arg Tyr Tyr Trp
        435                 440                 445
Gly Gly Gln Tyr Thr Trp Asp Met Ala Lys His Gly Thr Asp Asp Gly
    450                 455                 460
Val Val Trp Met Asn Trp Lys Gly Ser Trp Tyr Ser Met Arg Lys Met
465                 470                 475                 480
Ser Met Lys Ile Arg Pro Phe Phe Pro Gln Gln
                485                 490
```

```
<210> SEQ ID NO 12
<211> LENGTH: 15
<212> TYPE: PRT
<213> ORGANISM: Artificial Sequence
<220> FEATURE:
<223> OTHER INFORMATION: Citrullinated peptide
<220> FEATURE:
<221> NAME/KEY: misc_feature
<222> LOCATION: (1)..(1)
<223> OTHER INFORMATION: X = citrullyl or arginyl residue
<220> FEATURE:
<221> NAME/KEY: misc_feature
<222> LOCATION: (7)..(7)
<223> OTHER INFORMATION: X = citrullyl or arginyl residue
<220> FEATURE:
<221> NAME/KEY: misc_feature
<222> LOCATION: (10)..(10)
<223> OTHER INFORMATION: X = citrullyl or arginyl residue

<400> SEQUENCE: 12

Xaa Gly His Ala Lys Ser Xaa Pro Val Xaa Gly Ile His Thr Ser
 1               5                  10                  15
```

US 9,249,208 B2

CITRULLINE PEPTIDES DERIVED FROM FIBRIN AND RECOGNIZED BY RHEUMATOID ARTHRITIS SPECIFIC AUTOANTIBODIES, AND THE USE THEREOF

CROSS REFERENCE TO RELATED APPLICATIONS

This application is a divisional of U.S. application Ser. No. 11/577,674, filed Oct. 2, 2008, which is a 35 U.S.C. 371 national phase application of international application PCT/FR2005/002736 filed Nov. 3, 2005, which claim priority to French Application No. 04 11782, filed Nov. 4, 2004, French Application No. 04 13711, filed Dec. 22, 2004 and French Application No. 05 08422, filed Aug. 8, 2005, which are hereby incorporated herein in their entirety by reference.

FIELD AND BACKGROUND OF THE INVENTION

The present invention relates to novel citrullinated peptides recognized by rheumatoid arthritis-specific autoantibodies.

Rheumatoid arthritis (hereinafter abbreviated to "RA") is the most common of the chronic inflammatory forms of rheumatism. It is an autoimmune disease and the serum from affected patients contains autoantibodies, some of which are specific and may constitute a marker for this disease, allowing it to be diagnosed even at very early stages. Research studies have therefore been carried out for the purpose of identifying antigens recognized by these antibodies, in order to obtain purified preparations of the latter that can be used in conventional techniques of immunological diagnosis.

It has been shown that RA-specific autoantibodies recognize various isoelectric variants of (pro)filaggrin (for review, cf., for example, SERRE and VINCENT, In: Autoantibodies, PETER and SHOENFELD Eds, Elsevier Science Publishers, 271-276, 1996). These autoantibodies have for this reason been called: "anti-filaggrin autoantibodies (AFAs)". Application EP 0 511 116 describes the purification and characterization of antigens of the filaggrin family, recognized by these antibodies, and their use for the diagnosis of rheumatoid arthritis.

Subsequently, the filaggrin epitopes identified by AFAs were identified as regions of the filaggrin molecule carrying citrullyl residues, resulting from the conversion of arginyl residues by a peptidylarginine deiminase (Girbal-Neuhauser E et al., J. Immunol, 162, 585-94, 1999; Schellekens G A et al., J Clin Invest, 101, 273-81, 1998). The analysis of various synthetic peptides derived from the sequence of human filaggrin has shown that deimination (citrullination) is necessary in order to form the epitopes recognized by AFAs, which are today also called anti-citrullinated protein autoantibodies (ACPAs). It is this name that will be used in the disclosure which follows.

It has also been observed that the environment of the citrullyl residues also plays an important role (Girbal-Neuhauser E, 1999, mentioned above; Schellekens G A, 1998, mentioned above; Union A et al., Arthritis Rheum, 46, 1185-95, 2002); some amino acids that are "permissive" with respect to binding of the antibody, and the nature of which probably modifies the antibody binding affinity, have been identified. Among these amino acids, -gly-, -ser-, -his-, -thrand -gln- residues are most commonly found in the immediate environment of the citrullyl residues of citrullinated "filaggrin" peptides which, to date, have been identified as carrying epitopes recognized by ACPAs (Sebbag M et al., Rev Rhum, 68, 106, 2001).

A large number of citrullinated peptides specifically recognized by ACPAs, and that can be used for the diagnosis of RA, have been obtained from filaggrin. However, it has also been observed that, although strictly specific RA, the reactivity of these various citrullinated peptides with respect to ACPAs is heterogeneous, different peptides being recognized by sera derived from different individuals. This implies that, in order to obtain a diagnostic reagent capable of identifying the presence of ACPAs in a large population, it is necessary to combine several different peptides.

In parallel, it has been shown that ACPAs are secreted by synovial tissue plasma cells (Masson-Bessière C et al., Clin Exp Immunol, 119, 544-52, 2000) and are specifically directed against citrullinated forms of fibrin α- and β-chains present in this tissue (Masson-Bessière C et al., J Immunol, 166, 4177-84, 2001).

The inventors have undertaken, with the aim of more thoroughly characterizing the epitopes recognized by ACPAs, to identify those presented by fibrin α- and β-chains. For this purpose, they have evaluated the reactivity of sera containing ACPAs with respect to citrullinated synthetic peptides derived from the sequence of the α-chain and from the sequence of the β-chain of fibrin. Given the known heterogeneity of the reaction profiles of citrullinated peptides derived from filaggrin, with ACPAs, the inventors used mixtures of sera selected so as to contain ACPAs representing the various reactivity profiles observed in the case of these filaggrin-derived peptides, in order to detect all the fibrin peptides that may be recognized by ACPAs.

The peptides tested were obtained from the sequence of the α-chain and from the sequence of the β-chain of fibrin. In total, 72 peptides, including 41 derived from the fibrin α-chain and 31 derived from its β-chain, were selected. Among the 72 citrullinated peptides analyzed, the inventors identified 13 peptides derived from the sequence of the α-chain and 5 peptides derived from that of the α-chain of fibrin as reacting significantly with one and/or the other of the mixtures of sera tested, and therefore as carrying epitopes recognized by some of the ACPAs present in this of these mixture(s).

The inventors subsequently individually analyzed each of the 18 reactive peptides identified with each of the sera constituting the mixtures tested. This analysis confirmed, for most of the peptides tested, the large interindividual variability in ACPA specificity previously observed in the case of filaggrin-derived citrullinated peptides.

Furthermore, it allowed the inventors to identify peptides which, unexpectedly, have a spectrum of reactivity with ACPAs that is much broader than those reported up until now in the case of filaggrin-derived citrullinated peptides. Indeed, the inventors have identified 5 citrullinated peptides (4 peptides derived from the fibrin α-chain and 1 derived from the fibrin α-chain) which are each individually recognized by at least 40% of the sera analyzed, and therefore appear to carry major epitopes. Among these peptides, two are recognized by the majority of the sera, and also exhibit complementary reactivity profiles encompassing all the sera analyzed. Each of these sera in fact recognizes one and/or the other of these peptides. This suggests that these two peptides carry structural motifs representative of a very large majority of the various motifs recognized by ACPAs.

SUMMARY OF THE INVENTION

A subject of the present invention is an isolated peptide recognized by anti-citrullinated protein autoantibodies (ACPAs) present in the serum of patients suffering from rheumatoid arthritis, characterized in that it comprises at least one citrullyl residue, and in that it is chosen from the group consisting of:

a) a peptide defined by the sequence $X_1PAPPPISGGGYX_2AX_3$ (SEQ ID NO: 1) in which $X_1$ and $X_2$ each represent a citrullyl residue or an arginyl residue, and at least one of the residues $X_1$ and $X_2$ is a citrullyl residue;

b) a peptide defined by the sequence $GPX_1VVEX_2HQSACKDS$ (SEQ ID NO: 2) in which $X_1$ and $X_2$ each represent a citrullyl residue or an arginyl residue, and at least one of the residues $X_1$ and $X_2$ is a citrullyl residue;

c) a peptide defined by the sequence $SGIGTLDGFX_1HX_2HPD$ (SEQ ID NO: 3) in which $X_1$ and $X_2$ each represent a citrullyl residue or an arginyl residue, and at least one of the residues $X_1$ and $X_2$ is a citrullyl residue;

d) a peptide defined by the sequence $VDIDIKIX_1SCX_2GSCS$ (SEQ ID NO: 4) in which $X_1$ and $X_2$ each represent a citrullyl residue or an arginyl residue, and at least one of the residues $X_1$ and $X_2$ is a citrullyl residue;

e) a peptide defined by the sequence $X_1GHAKSX_2PVX_3GIHTS$ (SEQ ID NO: 12) in which $X_1$, $X_2$ and $X_3$ each represent a citrullyl residue or an arginyl residue, and at least one of the residues $X_1$, $X_2$ and $X_3$ is a citrullyl residue;

f) a peptide comprising at least 5 consecutive amino acids, preferably at least 7 consecutive amino acids, and advantageously from 8 to 14 consecutive amino acids, including at least one citrullyl residue, of one of the peptides a) to e) above.

BRIEF DESCRIPTION OF THE SEVERAL VIEWS OF THE DRAWINGS

Having thus described embodiments of the invention in general terms, reference will be made to that accompanying drawings wherein:

FIG. 1A illustrates SEQ ID NO: 10, which is that of a signal sequence; and

FIG. 1B illustrates SEQ ID NO: 11, which is that of a signal sequence.

DETAILED DESCRIPTION

The peptides in accordance with the invention are at least 5 amino acids in size, preferably from 5 to 25 amino acids in size, and entirely preferably from 10 to 20 amino acids in size.

According to a preferred embodiment of a peptide in accordance with the invention, it is chosen from:

a peptide defined by the sequence SEQ ID NO: 1 in which at least $X_3$ is a citrullyl residue, or a peptide comprising a fragment of at least 5 consecutive amino acids of said sequence containing said citrullyl residue;

a peptide defined by the sequence SEQ ID NO: 2 in which at least $X_2$ is a citrullyl residue, or a peptide comprising a fragment of at least 5 consecutive amino acids of said sequence containing said citrullyl residue;

a peptide defined by the sequence SEQ ID NO: 3 in which at least $X_2$ is a citrullyl residue, or a peptide comprising a fragment of at least 5 consecutive amino acids of said sequence containing said citrullyl residue;

a peptide defined by the sequence SEQ ID NO: 4 in which at least $X_1$ is a citrullyl residue, or a peptide comprising a fragment of at least 5 consecutive amino acids of said sequence containing said citrullyl residue;

a peptide defined by the sequence SEQ ID NO: 12 in which at least $X_3$ is a citrullyl residue, or a peptide comprising a fragment of at least 5 consecutive amino acids of said sequence containing said citrullyl residue.

Particularly preferably, a peptide in accordance with the invention is chosen from:

a peptide defined by the sequence SEQ ID NO: 1 in which $X_1$, $X_2$ and $X_3$ are citrullyl residues, or a peptide of at least 16 amino acids comprising said sequence;

a peptide defined by the sequence SEQ ID NO: 2 in which $X_1$ and $X_2$ are citrullyl residues, or a peptide comprising a fragment of at least 5 consecutive amino acids of said sequence containing said citrullyl residues;

a peptide defined by the sequence SEQ ID NO: 3 in which $X_1$ and $X_2$ are citrullyl residues, or a peptide comprising a fragment of at least 5 consecutive amino acids of said sequence containing said citrullyl residues;

a peptide defined by the sequence SEQ ID NO: 4 in which $X_1$ and $X_2$ are citrullyl residues, or a peptide comprising a fragment of at least 5 consecutive amino acids of said sequence containing said citrullyl residues;

a peptide defined by the sequence SEQ ID NO: 12 in which $X_1$, $X_2$ and $X_3$ are citrullyl residues, or a peptide comprising a fragment of at least 10 consecutive amino acids of said sequence containing said citrullyl residues.

Citrullinated peptides in accordance with the invention can, for example, be obtained from natural, recombinant or synthetic fragments of fibrin or of fibrinogen, through the action of peptidylarginine deiminase (PAD); they can also be obtained by peptide synthesis, by directly incorporating one or more citrulline residues into the peptide synthesized.

Citrullinated peptides in accordance with the invention also encompass derivatives of the peptides SEQ ID NOS: 1 to 4 and 12, or fragments thereof, defined above, said derivatives carrying modifications intended to improve recognition thereof by ACPAs: by way of examples of such derivatives, mention will be made of: cyclized peptides; retro-type peptides, in which L-amino acids are linked together according to a sequence that is the reverse of that of the peptide to be reproduced; retro-inverso-type peptides, consisting of amino acids of the D series (instead of the amino acids of the L series of natural peptides) linked together according to a sequence that is the reverse of that of the peptide to be reproduced.

Very advantageously, the peptides are peptides in which the terminal carboxyl function (COOH) is replaced with a carboxamide function ($CONH_2$). In this case, particularly preferred peptides are those in which the C-terminal residue is a citrullyl residue, the carboxyl function of which is replaced with a carboxamide function.

A subject of the present invention is also any peptide recognized by ACPAs present in the serum of patients suffering from rheumatoid arthritis, and containing, at its C-terminal end, a citrullyl residue, the carboxyl function of which is replaced with a carboxamide function. Advantageously, said peptide contains at least one other citrullyl residue in its sequence. Preferably, said peptide comprises from 5 to 25 amino acids.

The replacement of the carboxyl function of the C-terminal citrulline residue with a carboxamide function can make it possible to increase the reactivity of the peptide with the ACPAs, or, where appropriate, to render reactive, with ACPAs, peptides which are not naturally reactive.

Citrullinated peptides in accordance with the present invention also encompass derivatives of the peptides of SEQ ID NOS: 1 to 4 and 12, or fragments thereof, as defined above, said derivatives carrying modifications intended to facilitate their synthesis and/or to improve their stability. By way of example of such derivatives, mention will be made of the peptides that include amino acids, the carboxyl groups of which are esterified or converted to amide groups and/or amino acids, an amino group of which is alkylated, for example methylated or acetylated. The amine and carboxyl groups of the peptides may be present in the form of the salt corresponding to the base or to the acid.

From the citrullinated peptides described above, it is also possible to obtain mimotope peptides comprising at least one citrullyl residue (citrullinated mimotope peptide).

These mimotope peptides can be obtained by screening libraries of citrullinated peptides, the sequences of which are defined based on those of the peptides SEQ ID NOS: 1, 2, 3, 4 and 12 of the present invention, used in this context as "model peptides".

Preferably, these peptide libraries are prepared by synthesizing various peptides of between 10 and 20, preferably between 12 and 17, amino acids, in particular 15 amino acids in size. Each of these peptides conserves at least 2, preferably at least 4, advantageously at least 6, particularly preferably at least 8, and very advantageously at least 10 amino acids, including at least one citrullyl residue, of the sequence of the selected model peptide, at the same positions as on said model peptide, the other positions being variable.

These libraries can advantageously be screened as described in the examples hereinafter, and in particular using sera representative of various ACPA reactivity profiles, as defined in Example 1 hereinafter.

Methods for synthesizing mimotope peptides are well known in themselves. Reference will, for example, be made to Chapter 6 of "Chemical approaches to the synthesis of peptides and proteins", Paul Lloyd-Williams, Fernando Albericio and Ernest Giralt, CRC Press New York, 1997, "Peptide libraries", pages 237-270.

These citrullinated mimotope peptides can be used, alone or in combination with other citrullinated peptides, and preferably in combination with at least one of the other peptides of the invention, in a diagnostic test for RA, for recognizing ACPAs.

A subject of the present invention is also the use of the peptides in accordance with the invention, as defined above, for detecting the presence of ACPAs in a biological sample, in the context of the in vitro diagnosis of RA.

A subject of the present invention is thus antigenic compositions that can be used for detecting the presence of ACPAs in a biological sample in the context of the in vitro diagnosis of RA, which compositions are characterized in that they comprise at least one peptide in accordance with the invention.

Compositions in accordance with the invention can associate with one another various peptides chosen from the peptides in accordance with the invention, or can associate one or more peptides in accordance with the invention with one or more citrullinated peptides derived, in particular, from filaggrin.

According to a preferred embodiment of an antigenic composition in accordance with the invention, it comprises at least one peptide of sequence SEQ ID NO: 1, and at least one peptide of sequence SEQ ID NO: 2, as defined above.

This composition has a very broad spectrum of reactivity, and can also make it possible to detect RA at an early stage.

Advantageously, a composition in accordance with the invention can also comprise a peptide of sequence SEQ ID NO: 3 and/or a peptide of sequence SEQ ID NO: 4 and/or a peptide of sequence SEQ ID NO: 12, as defined above.

The compositions in accordance with the invention can, where appropriate, be in the form of multiple-peptide compositions, in which the constitutive peptides are associated with one another or with a carrier molecule, generally by covalent bonding. By way of example, mention will be made of the multiple antigen peptides (MAPs) described in particular by TAM (Proc. Natl. Acad. Sci. U.S.A., 85, 5409-13, 1988).

A subject of the present invention is also a method for detecting the presence of ACPAs in a biological sample, in the context of the in vitro diagnosis of RA, which method is characterized in that it comprises:
  bringing said biological sample into contact with at least one peptide or one antigenic composition in accordance with the invention, as defined above, under conditions that allow the formation of an antigen/antibody complex with the ACPAs possibly present in said sample;
  detecting, by any appropriate means, the antigen/antibody complex possibly formed.

This method of detection can be carried out by means of a kit comprising at least one peptide or one antigenic composition according to the invention and, where appropriate, buffers and reagents suitable for making up a reaction medium that allows the formation of an antigen/antibody complex, and/or means for detecting said antigen/antibody complex.

Advantageously, said kit comprises a peptide or an antigenic composition according to the invention, immobilized on a solid substrate. By way of nonlimiting examples of solid substrates that can be used, mention will be made of microtitration plates, pipette tips of the VIDAS® device (sold by BIOMERIEUX), beads, microbeads or microparticles, strips, etc.

Said kit can also comprise reference samples, such as one or more negative serum or sera and one or more positive serum or sera.

A subject of the present invention is also a method for detecting the presence of ACPAs in a biological sample, in the context of the in vitro diagnosis of RA, which method is characterized in that it comprises:
  providing a first citrullinated peptide capable of competing, for the binding to said ACPAs, with a peptide in accordance with the invention, as defined above;
  bringing said first peptide into contact with said biological sample, under conditions that allow the formation of an antigen/antibody complex with the ACPAs possibly present in said sample;
  detecting, by any appropriate means, the antigen/antibody complex possibly formed.

In particular, the first citrullinated peptide capable of competing with a peptide in accordance with the invention is a citrullinated mimotope peptide that can be obtained as described above.

The present invention will be understood more clearly from the further description which follows, which makes reference to examples that illustrate the identification of the peptides in accordance with the invention and the demonstration of their reactivity profile with respect to ACPAs.

EXAMPLE 1

Demonstration of the Heterogeneity of the Reaction of Acpas with Citrullinated Peptides Derived from Filaggrin, and Obtaining of Mixtures of Sera Representative of the Various Reactivity Profiles 90 sera, exhibiting ACPAs that can be detected both by ELISA and by immunoblotting on human fibrinogen deiminated in vitro (Masson-Bessière C, 2001, mentioned above; Nogueira L et al., Arthritis Res, 4, 90, 2002) but also by indirect immunofluoresence on frozen sections of rat esophagus (Vincent C et al., Ann Rheum Dis, 48, 712-22, 1989) and by immunoblotting on human epidermal filaggrin (Vincent C et al., J Rheumatol, 25, 838-46, 1998), were used. The reactivity of these 90 multipositive sera was analyzed by ELISA with regard to 5 different citrullinated peptides, the reactivity of which with respect to ACPAs had been previously established. These peptides are the following:

| | | |
|---|---|---|
| E12D | ESSRDGSXHPRSHD | (SEQ ID NO: 5) |
| T12E | TGSSTGGXQGSHHE | (SEQ ID NO: 6) |
| E12H | EQSADSSXHSGSGH | (SEQ ID NO: 7) |
| cfc6 | SHQESTXGXSRGRSGRSGS | (SEQ ID NO: 8) |
| cf48-65-4 | TIHAHPGSXXGGRHGYHH | (SEQ ID NO: 9) |

(X denotes a citrullyl residue)

The peptides E12D, T12E and E12H were described by Girbal-Neuhauser, E. et al. (1999), the peptides cfc6 and cf48-65-4 were described by Schellekens, G. et al. (1998).

The analysis by ELISA was carried out according to the protocol described by Girbal-Neuhauser, E. et al. (1999).

This analysis made it possible to identify 12 reactivity profiles with regard to the 5 peptides.

These profiles are summarized in Table I below.

TABLE I

| Profile | E12D | E12H | T12E | cfc6 | cf48-65-4 |
|---|---|---|---|---|---|
| 1 | + | + | + | | + |
| 2 | + | + | + | | |
| 3 | + | + | | + | |
| 4 | + | + | | | |
| 5 | + | | | | |
| 6 | + | | | | + |
| 7 | | + | | | |
| 8 | | + | + | | + |
| 9 | | | + | | |
| 10 | | | | + | + |
| 11 | | | + | | |
| 12 | | | | | + |

In order to be as representative as possible of the various ACPA reactivity profiles, mixtures, hereinafter referred to as mixtures: "A" and "B", were each formed by mixing, in equal parts, 10 sera representing various profiles of reactivity on "filaggrin" peptides.

The composition of these two mixtures is given in Table II below.

TABLE II

| Serum | Profile | Mixture |
|---|---|---|
| 97.0459 | 1 | A |
| 97.0388 | 3 | |
| 97.1436 | 4 | |
| 97.0169 | 6 | |
| 97.0530 | 7 | |

TABLE II-continued

| Serum | Profile | Mixture |
|---|---|---|
| 97.0311 | 8 | |
| 97.0506 | 9 | |
| 97.0468 | 10 | |
| 97.0796 | 11 | |
| 97.0907 | 12 | |
| 97.1715 | 1 | B |
| 97.0524 | 1 | |
| 97.0323 | 2 | |
| 97.0794 | 4 | |
| 95.0256 | 5 | |
| 97.1795 | 5 | |
| 97.1474 | 9 | |
| 97.0244 | 10 | |
| 97.1548 | 11 | |
| 97.1210 | 12 | |

The two mixtures A and B together are therefore representative of the heterogeneity of specificity of the ACPA+ sera.

EXAMPLE 2

Identification of Citrullinated Peptides Derived From Fibrin α- and β-Chains, that React with the ACPAs The peptides tested were obtained from the sequence of the fibrin α-chain and from the sequence of the fibrin β-chain [portion corresponding respectively to residues 36-635 and 45-491 of the A(α) (reference NP Acession: NP 068657) and B(β) (reference SWISSPROT FIBS_HUMAN Prim. Accession: P02675) chains of fibrinogen]. The sequences of residues 1 to 635 and 1 to 491 of the fibrinogen A(α) and B(β) chains are also respectively represented in the attached sequence listing under the numbers SEQ ID NO: 10 and SEQ ID NO: 11, and in FIGS. 1A and B. The sequences indicated in bold in FIG. 1 are those of the signal sequences of the proteins followed by those of their fibrinopeptides (A and B, respectively).

Each fibrin α- or β-chain was segmented into contiguous sequences of 15 amino acids, and all the peptides comprising at least one arginyl residue were selected. In the case of the peptides for which the arginyl residue was located at the $NH_2$— or COON-terminal end, a second series of peptides of 15 amino acids, overlapping the first, so as to recenter the terminal arginyl residue in the sequence, was selected. In addition, a peptide corresponding to residues 621-629 of the fibrin α-chain was synthesized. In total, 72 peptides, including 41 derived from the fibrin α-chain and 31 derived from its β-chain, were selected. For each of the peptides, the form with arginyl residue(s) (native form) and the form where all the arginyl residues were substituted with citrullyl residues (citrullinated form) were synthesized according to the solid-phase method of Merrifield, with a purity ≥60% [company NeoMPS (Strasbourg, France)].

The list of the citrullinated peptides selected is given in Table III below:

TABLE III

A. First series:

α-chain

| | | | |
|---|---|---|---|
| α36-50$Cit_{38,42}$ | α171-185$Cit_{178,181}$ | α351-365$Cit_{353}$ | α456-470$Cit_{458,459}$ |
| α66-80$Cit_{58}$ | α186-200$Cit_{186,190}$ | α366-380$Cit_{367}$ | α501-515$Cit_{510,512}$ |
| α81-95$Cit_{84}$ | α216-230$Cit_{216,218}$ | α381-395$Cit_{394}$ | α546-560$Cit_{547}$ |
| α111-125$Cit_{114,123}$ | α246-260$Cit_{258}$ | α396-410$Cit_{404}$ | α561-575$Cit_{573}$ |
| α126-140$Cit_{129,135,137}$ | α261-275$Cit_{263,271}$ | α411-425$Cit_{425}$ | α591-605$Cit_{591}$ |

TABLE III-continued

| α141-155Cit$_{143}$ | α276-290Cit$_{287}$ | α426-440Cit$_{426}$ | α621-629Cit$_{621,627}$ |
| α156-170Cit$_{160,168}$ | α306-320Cit$_{308}$ | α441-455Cit$_{443}$ | α621-635Cit$_{621,627,630}$ |

β-chain

| β45-59Cit$_{47,53}$ | β195-209Cit$_{196,199,208}$ | β330-344Cit$_{334}$ | β435-449Cit$_{436,445}$ |
| β60-74Cit$_{60,72,74}$$^a$ | β210-224Cit$_{224}$ | β375-389Cit$_{376}$ | β465-479Cit$_{478}$ |
| β75-89Cit$_{87}$ | β240-254Cit$_{246}$ | β390-404Cit$_{395}$ | β480-491Cit$_{485}$ |
| β120-134Cit$_{121,124}$ | β255-269Cit$_{267}$ | β405-419Cit$_{410}$ | |
| β150-164Cit$_{158}$ | β285-299Cit$_{286,284}$ | β420-434Cit$_{421}$ | |

B. Second series:

α-chain

| α138-152Cit$_{143}$ | α300-314Cit$_{308}$ | α438-452Cit$_{443}$ | α615-629Cit$_{621,627}$ |
| α183-197Cit$_{186,190}$ | α347-361Cit$_{353}$ | α455-469Cit$_{458,459}$ | |
| α213-227Cit$_{216,218}$ | α363-377Cit$_{367}$ | α542-556Cit$_{547}$ | |
| α259-273Cit$_{263,271}$ | α420-434Cit$_{425,426}$ | α588-602Cit$_{591}$ | |

β-chain

| β50-64Cit$_{53,60}$ | β202-216Cit$_{206}$ | β281-295Cit$_{285,294}$ | β474-488Cit$_{478,485}$ |
| β116-130Cit$_{121,124}$ | β215-229Cit$_{224}$ | β373-387Cit$_{376}$ | |
| β188-202Cit$_{196,199}$ | β219-233Cit$_{224}$ | β416-430Cit$_{421}$ | |
| β193-207Cit$_{195,199,206}$ | β236-250Cit$_{246}$ | β433-447Cit$_{436,445}$ | |

$^a$This peptide was synthesized with the carboxyl function (COOH) of the C-terminal citrullyl residue either in "free" form (COOH), or in amidated form (carboxamide function: CONH$_2$).

The nomenclature used is the following: name of origin of the polypeptide chain (α or β) of fibrinogen from which the sequence derives, then position in this sequence of the amino-terminal residue of the peptide—position of the carboxy-terminal residue of the peptide. These positions are numbered relative to the N-terminal end of fibrinogen. The designation Cit indicates that it is a citrullinated form of the peptide. The position of the arginyl residue which is substituted with a citrullyl residue is indicated as an index. Only the citrullinated forms of the peptides are presented.

Each pair of peptides (citrullinated and noncitrullinated) was assayed by ELISA with a mixture, in equal parts, of 10 sera having no ACPAs (control mixture) and with the 2 mixtures A and B described in Example 1.

The peptides were tested after coating of irradiated polystyrene plates (Nunc Maxisorp) in three different buffers (acetate, pH 5.0; PBS, pH 7.4; and carbonate, pH 9.0), so as to optimize the chances of passive binding of the peptides (10 μg/ml) that exhibited very heterogeneous isoelectric points (extending from 4 to 12 for the noncitrullinated forms). Each pair of peptides (native and citrullinated form) was tested on the same plate and a pair of control peptides—citrullinated "filaggrin" peptide cfc6 and its corresponding native peptide cf0 (Schellekens G A, 1998, mentioned above)—was included in each experiment, which made it possible to calculate an inter-assay coefficient of variation and to perform corrections.

After saturation in PBS-2% BSA, the mixtures of sera diluted to 1/50 in PBS 2M NaCl—2% BSA were incubated and then their binding was revealed with peroxidase-labeled anti-human IgG goat IgGs (Southern) diluted to 1/1000 in PBS-2% BSA. All the incubations were carried out for 1 h at 4° C. and were followed by washing in PBS-0.1% Tween. The peroxidase activity was visualized with a solution of ortho-phenylenediamine (2 mg/ml—Sigma) in hydrogen peroxide (0.03%—Sigma). The reaction was stopped after 5 minutes by adding 4M sulfuric acid, and the optical density (OD) at 492 nm was measured by virtue of an automatic spectrophotometer (Multiskan, Thermo Labsystems).

The specific reactivity of the mixtures of sera with regard to the citrullinated peptides corresponded to the difference between the OD obtained with the citrullinated peptide and that obtained with the corresponding native peptide (delta OD). The results correspond to the mean of two determinations. Any citrullinated peptide making it possible to obtain a delta OD of greater than 0.250 for at least one of the two mixtures A and B after coating in at least one of the three buffers, was considered to be reactive.

Among the 72 citrullinated peptides analyzed, 13 peptides derived from the sequence of the fibrin α-chain and 5 peptides derived from that of the β-chain were found to carry epitopes recognized by the ACPAs. Among these peptides, 6 were very reactive (delta OD≥1.5), 8 peptides were moderately reactive (0.5≤delta OD<1.5) and 4 peptides were relatively nonreactive (0.25≤delta OD<0.5). The other citrullinated peptides prove to be barely reactive or nonreactive (0.0≤delta OD<0.25). No reactivity with the control mixture was observed, which makes it possible to identify the reactive peptides as carriers of epitope(s) recognized by the ACPAs.

The results obtained for the 18 reactive peptides are given in Table IV below:

TABLE IV

| Peptide | Mixture of sera | Coating buffer | | |
| --- | --- | --- | --- | --- |
| | | Acetate | PBS | Carbonate |
| α36-50Cit$_{38,42}$ | Mixture A | 4.00 | 2.69 | 3.43 |
| | Mixture B | 4.27 | 2.65 | 2.64 |
| α171-185Cit$_{178,181}$ | Mixture A | 0.15 | 0.29 | 0.75 |
| | Mixture B | 0.08 | 0.21 | 0.47 |
| α183-197Cit$_{186,190}$ | Mixture A | 0.41 | 1.68 | 1.36 |
| | Mixture B | 0.01 | 0.15 | 0.07 |
| α246-260Cit$_{258}$ | Mixture A | 0.04 | 0.00 | 0.00 |
| | Mixture B | 0.27 | 0.25 | 0.33 |
| α259-273Cit$_{263,271}$ | Mixture A | 0.14 | 0.60 | 0.12 |
| | Mixture B | 0.21 | 0.69 | 0.20 |
| α366-380Cit$_{367}$ | Mixture A | 0.28 | 0.37 | 0.26 |
| | Mixture B | 0.00 | 0.04 | 0.08 |
| α396-410Cit$_{404}$ | Mixture A | 0.04 | 0.02 | 0.43 |
| | Mixture B | 0.15 | 0.17 | 0.20 |
| α411-425Cit$_{425}$ | Mixture A | 0.09 | 0.16 | 0.56 |
| | Mixture B | 0.38 | 0.66 | 0.43 |
| α501-515Cit$_{510,512}$ | Mixture A | 0.16 | 0.92 | 0.15 |
| | Mixture B | 0.72 | 2.60 | 0.79 |
| α546-560Cit$_{547}$ | Mixture A | 0.38 | 0.74 | 0.33 |
| | Mixture B | 0.05 | 0.15 | 0.16 |

TABLE IV-continued

| Peptide | Mixture of sera | Coating buffer | | |
|---|---|---|---|---|
| | | Acetate | PBS | Carbonate |
| α561-575Cit$_{573}$ | Mixture A | 0.05 | 0.30 | 0.01 |
| | Mixture B | 0.14 | 0.52 | 0.17 |
| α588-602Cit$_{591}$ | Mixture A | 0.05 | 0.16 | 0.36 |
| | Mixture B | 0.06 | 0.33 | 0.67 |
| α621-635Cit$_{621,627,630}$ | Mixture A | 0.25 | 1.57 | 1.17 |
| | Mixture B | 0.18 | 1.51 | 1.20 |
| β60-74Cit$_{60,72,74}$[a] | Mixture A | 1.02 | 2.06 | 1.27 |
| | Mixture B | 2.83 | 2.69 | 2.72 |
| β210-224Cit$_{224}$ | Mixture A | 0.25 | 0.29 | 1.14 |
| | Mixture B | 0.00 | 0.60 | 1.56 |
| β281-295Cit$_{285,294}$ | Mixture A | 0.12 | 0.60 | 0.61 |
| | Mixture B | 0.11 | 0.75 | 0.71 |
| β420-434Cit$_{421}$ | Mixture A | 0.36 | 0.48 | 0.44 |
| | Mixture B | 0.00 | 0.00 | 0.00 |
| β433-447Cit$_{435,445}$ | Mixture A | 0.41 | 0.58 | 0.67 |
| | Mixture B | 0.00 | 0.00 | 0.03 |

[a]The results indicated correspond to those obtained with the form of the peptide having an amidated C-terminal function (carboxamide function: CONH$_2$)

EXAMPLE 3

Reactivity Profile of the Citrullinated Peptides that React with the ACPAs

The 14 peptides carrying the most reactive epitopes (delta OD≥0.5 for one or other of the mixtures of serum (A and B) with at least one of the three coating buffers) were tested independently with the 20 sera constituting the mixtures A and B, in order to evaluate the reactivity profile of each of these peptides. The tests were carried out by ELISA under the same conditions as in Example 2 above, with the exception that, for each pair of peptides, the coating buffer selected was that that had made it possible to obtain the strongest reactivity with respect to this peptide during the screening (the buffer for which the sum of the delta ODs obtained respectively for the serum mixtures A and B was at a maximum). In addition, the dilutions of the sera were adjusted such that they had an equivalent avidity for whole deiminated fibrinogen. Thus, for each serum, the dilution that made it possible to obtain an OD of 1 by ELISA on deiminated fibrinogen was selected (Nogueira L, 2002, mentioned above). The dilutions ranged from 1/20 to 1/2700.

The results are illustrated by Table V below.

TABLE V

| Serum | Dilution | β60-74Cit$_{60,72,74}$[a] | α36-50Cit$_{36,42}$ | α621-635Cit$_{621,627,630}$ | α501-515Cit$_{510,512}$ | α171-185Cit$_{178,181}$ |
|---|---|---|---|---|---|---|
| 97.0459 | 1/60 | 0.71[c] | 3.55 | | | 0.29 |
| 97.1715 | 1/300 | | 3.50 | | 1.79 | |
| 97.0524 | 1/200 | | 3.39 | | 2.85 | 0.59 |
| 97.0323 | 1/120 | 1.73 | 1.87 | | 3.23 | |
| 97.0388 | 1/50 | | 3.32 | 2.71 | 2.88 | |
| 97.1436 | 1/150 | | 3.30 | | 2.80 | |
| 97.0794 | 1/50 | 0.75 | 3.43 | | 3.30 | 2.09 |
| 95.0256 | 1/35 | 3.48 | 2.35 | | 2.37 | |
| 97.1795 | 1/50 | | 2.29 | | | 0.57 |
| 97.0169 | 1/400 | 0.31 | | 0.80 | | |
| 97.0530 | 1/50 | | 2.97 | | 0.69 | |
| 97.0311 | 1/200 | 1.93 | 0.71 | 0.37 | | 1.95 |
| 97.0506 | 1/75 | 1.93 | | | 0.44 | |
| 97.1474 | 1/20 | 0.37 | 1.93 | 0.59 | | 1.08 |
| 97.0468 | 1/700 | 1.08 | | 0.81 | | 0.42 |
| 97.0244 | 1/2700 | 1.23 | | 0.50 | | |
| 97.1548 | 1/60 | 1.48 | | 3.29 | | 0.71 |
| 97.0796 | 1/500 | 0.36 | | 0.69 | | |
| 97.0907 | 1/300 | 1.17 | | 1.04 | | 0.44 |
| 97.1210 | 1/300 | 3.33 | | 0.37 | | |
| Number of positive sera | | 14/20 | 12/20 | 10/20 | 9/20 | 9/20 |

| Serum | Dilution | β281-295Cit$_{285,294}$ | β210-224Cit$_{224}$ | α183-197Cit$_{186,190}$[b] | α561-575Cit$_{573}$ | α546-560Cit$_{547}$[b] |
|---|---|---|---|---|---|---|
| 97.0459 | 1/60 | 2.22 | | 3.21 | 0.38 | |
| 97.1715 | 1/300 | | | | | |
| 97.0524 | 1/200 | 0.25 | | | | |
| 97.0323 | 1/120 | 1.16 | 0.36 | | | |
| 97.0388 | 1/50 | | | | | |
| 97.1436 | 1/150 | | | | | |
| 97.0794 | 1/50 | 0.26 | | | 1.95 | |
| 95.0256 | 1/35 | | | | | |
| 97.1795 | 1/50 | | 0.49 | | | |
| 97.0169 | 1/400 | | | | | |
| 97.0530 | 1/50 | | | | | 0.44 |
| 97.0311 | 1/200 | | 0.46 | 0.87 | 0.30 | |
| 97.0506 | 1/75 | 1.80 | | 0.85 | | |
| 97.1474 | 1/20 | 0.36 | | | 0.71 | |
| 97.0468 | 1/700 | | | | | |
| 97.0244 | 1/2700 | | | | | |
| 97.1548 | 1/60 | | | | 0.53 | |
| 97.0796 | 1/500 | | 0.67 | | | 1.18 |
| 97.0907 | 1/300 | | 0.33 | | | |
| 97.1210 | 1/300 | | 0.72 | | | |
| Number of positive sera | | 6/20 | 6/20 | 3/10 | 5/20 | 2/10 |

TABLE V-continued

| Serum | Dilution | β433-447Cit$_{436,445}$[b] | α259-273Cit$_{263,271}$ | α588-602Cit$_{591}$ | α411-425Cit$_{425}$ |
|---|---|---|---|---|---|
| 97.0459 | 1/60 | | | | |
| 97.1715 | 1/300 | | | | |
| 97.0524 | 1/200 | | | | |
| 97.0323 | 1/120 | | | | |
| 97.0388 | 1/50 | 1.14 | | | |
| 97.1436 | 1/150 | | | | |
| 97.0794 | 1/50 | | | | |
| 95.0256 | 1/35 | | | | |
| 97.1795 | 1/50 | | | 0.79 | |
| 97.0169 | 1/400 | | | 1.34 | |
| 97.0530 | 1/50 | | | | |
| 97.0311 | 1/200 | | 0.29 | | |
| 97.0506 | 1/75 | | | | |
| 97.1474 | 1/20 | | 0.39 | | |
| 97.0468 | 1/700 | | 0.32 | | |
| 97.0244 | 1/2700 | | | | |
| 97.1548 | 1/60 | | | | |
| 97.0796 | 1/500 | 0.71 | | | |
| 97.0907 | 1/300 | | | | |
| 97.1210 | 1/300 | | | | 0.84 |
| Number of positive sera | | 2/10 | 13/20 | 2/20 | 1/20 |

[a]The results indicated correspond to those obtained with the form of the peptide having an amidated C-terminal function (carboxamide function: $CONH_2$).
[b]For these three peptides, the individual reactivity of the sera of mixture B was not tested since the latter was not reactive.
[c]The delta ODs <0.25 are not presented.

EXAMPLE 4

Comparison of the Reactivity of the Peptide β60-74Cit$_{60,72,74}$ Depending on Whether Its C-Terminal Function is a Carboxyl (COOH) or a Carboxamide ($CONH_2$)

ELISA plates were coated with the peptide β60-74Cit$_{60,72,74}$, in which the C-terminal function of the carboxy-terminal citrullyl residue is not amidated (form carrying a terminal COOH function, hereinafter referred to as "nonamidated form"), with the peptide β360-74Cit$_{60,72,74}$, in which the C-terminal function of the carboxy-terminal citrullyl residue is amidated (form carrying a terminal $CONH_2$ function, hereinafter referred to as "amidated form") and the noncitrullinated peptide β60-74 (in which the C-terminal function of the carboxy-terminal arginyl residue is not amidated), all diluted in PBS. The serum mixtures A and B described in Example 1 were tested according to the method described in Example 2.

As in Example 2, the specific reactivity of the peptide in nonamidated form or in amidated form corresponded to the difference between the OD obtained with these two citrullinated peptides and that obtained with the noncitrullinated peptide β60-74. The reactivity of the amidated form of the peptide appeared to be clearly greater than that of the nonamidated form, which was, however, significant. The results correspond to the mean of two experiments, each comprising two determinations. The results are given in Table VI below.

TABLE VI

| Peptide | Serum mixture | Delta OD |
|---|---|---|
| β60-74Cit$_{60, 72, 74}$ nonamidated | Mixture A | 0.30 |
| | Mixture B | 1.16 |
| β60-74Cit$_{60, 72, 74}$ amidated | Mixture A | 2.13 |
| | Mixture B | 2.74 |

What is claimed is:

1. A method for detecting the presence of ACPAs in a biological sample comprising:
   bringing said biological sample into contact with at least one peptide chosen from the group consisting of:
   a peptide consisting of the sequence $X_1$PAPPPISGGGY$X_2$A$X_3$ (SEQ ID NO: 1) in which $X_1$, $X_2$ and $X_3$ each represent a citrullyl residue or an arginyl residue, and at least one of the residues $X_2$ and $X_3$ is a citrullyl residue; and
   a peptide of 5 to 25 amino acids comprising a fragment of at least 5 consecutive amino acids of the peptide consisting of SEQ ID NO: 1, including at least $X_2$ or $X_3$ as a citrullyl residue, or
   an antigenic composition comprising said at least one peptide under conditions that allow the formation of an antigen/antibody complex with the ACPAs possibly present in said sample;
   detecting the antigen/antibody complex possibly formed.

2. A method for detecting the presence of ACPAs in a biological sample comprises:
   providing a first citrullinated peptide capable of competing, for the binding to said ACPAs, with a peptide chosen from the group consisting of:
   a peptide consisting of the sequence $X_1$PAPPPISGGGY$X_2$A$X_3$ (SEQ ID NO: 1) in which $X_1$, $X_2$ and $X_3$ each represent a citrullyl residue or an arginyl residue, and at least one of the residues $X_2$ and $X_3$ is a citrullyl residue; and
   a peptide of 5 to 25 amino acids comprising a fragment of at least 5 consecutive amino acids of the peptide consisting of SEQ ID NO: 1, including at least $X_2$ or $X_3$ as a citrullyl residue;
   bringing said first peptide into contact with said biological sample under conditions that allow the formation of an antigen/antibody complex with the ACPAs possibly present in said sample;
   detecting the antigen/antibody complex possibly formed.

3. The method of claim 1, wherein said peptide is chosen from the group consisting of a peptide consisting of SEQ ID NO: 1 in which at least $X_3$ is a citrullyl residue; and a peptide of 5 to 25 amino acids comprising a fragment of at least 5 consecutive amino acids of the peptide consisting of SEQ ID NO: 1, including at least $X_3$ as a citrullyl residue.

4. The method of claim 1, wherein said peptide is chosen from the group consisting of a peptide consisting of SEQ ID NO: 1 in which at least $X_2$ and $X_3$ are citrullyl residues; and a peptide of 5 to 25 amino acids comprising a fragment of at least 5 consecutive amino acids of the peptide consisting of SEQ ID NO: 1, including at least $X_2$ and $X_3$ as citrullyl residues.

5. The method of claim 1, wherein said peptide is chosen from the group consisting of a peptide consisting of SEQ ID NO: 1 in which $X_1$, $X_2$ and $X_3$ are citrullyl residues; and a peptide of 16 to 25 amino acids comprising said sequence, including $X_1$, $X_2$ and $X_3$ as citrullyl residues.

6. The method of claim 1, wherein the terminal carboxyl function (COOH) of said peptite is replaced with a carboxamide function ($CONH_2$).

7. The method of claim 2, wherein said peptide is chosen from the group consisting of a peptide consisting of SEQ ID NO: 1 in which at least $X_3$ is a citrullyl residue; and a peptide of 5 to 25 amino acids comprising a fragment of at least 5 consecutive amino acids of the peptide consisting of SEQ ID NO: 1, including at least $X_3$ as a citrullyl residue.

8. The method of claim 2, wherein said peptide is chosen from the group consisting of a peptide consisting of SEQ ID NO: 1 in which at least $X_2$ and $X_3$ are citrullyl residues; and a peptide of 5 to 25 amino acids comprising a fragment of at least 5 consecutive amino acids of the peptide consisting of SEQ ID NO: 1, including at least $X_2$ and $X_3$ as citrullyl residues.

9. The method of claim 1, wherein said peptide is chosen from the group consisting of a peptide consisting of SEQ ID NO: 1 in which $X_1$, $X_2$ and $X_3$ are citrullyl residues; and a peptide of 16 to 25 amino acids comprising said sequence, including $X_1$, $X_2$ and $X_3$ as citrullyl residues.

10. The method of claim 2, wherein the terminal carboxyl function (COOH) of said peptite is replaced with a carboxamide function ($CONH_2$).

* * * * *

UNITED STATES PATENT AND TRADEMARK OFFICE
CERTIFICATE OF CORRECTION

PATENT NO. : 9,249,208 B2
APPLICATION NO. : 13/489072
DATED : February 2, 2016
INVENTOR(S) : Serre et al.

Page 1 of 1

It is certified that error appears in the above-identified patent and that said Letters Patent is hereby corrected as shown below:

In the claims:

Column 25,
Line 45, "comprises" should read --comprising--.

Column 26,
Line 57, "The method of claim 1" should read --The method of claim 2--.

Signed and Sealed this
Twenty-first Day of June, 2016

Michelle K. Lee
*Director of the United States Patent and Trademark Office*